United States Patent
Matsunaga

(10) Patent No.: US 9,493,418 B2
(45) Date of Patent: Nov. 15, 2016

(54) METHOD FOR PRODUCING PURIFIED AMINE COMPOUND

(71) Applicant: SUMITOMO CHEMICAL COMPANY, LIMITED, Tokyo (JP)

(72) Inventor: Tadafumi Matsunaga, Oita (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/649,592

(22) PCT Filed: Dec. 11, 2013

(86) PCT No.: PCT/JP2013/083806
§ 371 (c)(1),
(2) Date: Jun. 4, 2015

(87) PCT Pub. No.: WO2014/103811
PCT Pub. Date: Jul. 3, 2014

(65) Prior Publication Data
US 2015/0344431 A1   Dec. 3, 2015

(30) Foreign Application Priority Data
Dec. 27, 2012 (JP) .................. 2012-284309

(51) Int. Cl.
C07C 211/60 (2006.01)
C07D 215/04 (2006.01)
C07C 209/84 (2006.01)
C07D 215/06 (2006.01)

(52) U.S. Cl.
CPC ........... *C07D 215/06* (2013.01); *C07C 209/84* (2013.01); *C07C 211/60* (2013.01); *C07D 215/04* (2013.01)

(58) Field of Classification Search
CPC ............ C07D 215/06; C07D 215/041; C07C 211/60; C07C 209/84
USPC ......................................................... 546/181
See application file for complete search history.

(56) References Cited

U.S. PATENT DOCUMENTS

| 2,514,648 A | 7/1950 | Kehe |
| 5,710,315 A | 1/1998 | Gallagher |
| 9,227,911 B2 * | 1/2016 | Ujita .................... C07C 51/412 |
| 2008/0249200 A1 | 10/2008 | Yokoyama et al. |
| 2015/0203438 A1 * | 7/2015 | Ujita .................... C07C 59/255 564/304 |
| 2015/0266805 A1 * | 9/2015 | Takahashi ............... C07B 55/00 564/302 |

FOREIGN PATENT DOCUMENTS

| DE | 1957 259 | 5/1971 |
| DE | 1957259 A1 | 5/1971 |
| DE | 42 03 481 A1 | 11/1993 |
| DE | 4203481 A1 | 11/1993 |
| EP | 0654464 A1 | 5/1995 |
| JP | 48-11103 | 4/1973 |
| JP | 48-11103 B1 | 4/1973 |
| JP | 52-108991 A | 9/1977 |
| JP | 4-54173 A | 2/1992 |
| JP | 7-215921 A | 8/1995 |
| JP | 52-108991 | 9/1997 |
| JP | 2002-507187 A | 3/2002 |
| JP | 2012-214437 A | 11/2012 |
| WO | WO 2006/093122 A1 | 9/2006 |
| WO | WO2011162397 | * 12/2011 |

OTHER PUBLICATIONS

Kolodkina; Zhurnal Obshchei Khimii, 1963, 33, 469-474, Abstract from Chemical Abstracts.*
Elwahy; Tetrahedron Letters 2006 47 1303-1306.*
International Search Report issued in PCT/JP2013/083806, mailed on Mar. 25, 2014.
Cliffe et al., "The Acid-catalysed Rearrangement of Tetrahydroquinoline Derivatives," Journal of the Chemical Society, 1966, pp. 514-517.
International Preliminary Report on Patentability and Written Opinion of the International Searching Authority (Forms PCT/IB/373 and PCT/ISA/237) for International Application No. PCT/JP2013/083806, dated Jun. 30, 2015.
Craig, "The Reaction of Acetone with Aniline," Journal of the American Chemical Society, vol. 60, No. 6, Jun. 1938, pp. 1458-1465, XP002756893.
Extended European Search Report, dated May 10, 2016, for European Application No. 13868569.8.

* cited by examiner

*Primary Examiner* — Noble Jarrell
*Assistant Examiner* — Daniel Carcanague
(74) *Attorney, Agent, or Firm* — Birch, Stewart, Kolasch & Birch, LLP

(57) ABSTRACT

A method for producing a purified amine compound represented by the formula (1), including: step (A) of reacting a crude form of the amine compound represented by the formula (1) with a hydrogen halide in the presence of water and an organic solvent insoluble in water; step (B) of separating a phase in which a hydrogen halide salt of the amine compound represented by the formula (1) produced in step (A) is dissolved from the other phase(es); step (C) of precipitating the hydrogen halide salt of the amine compound represented by the formula (1) from the phase obtained in step (B) in which the hydrogen halide salt of the amine compound represented by the formula (1) is dissolved; and step (D) of isolating the hydrogen halide salt of the amine compound represented by the formula (1) precipitated in step (C), and reacting the salt with a base.

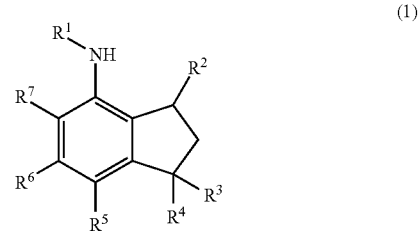

(1)

4 Claims, No Drawings

100
METHOD FOR PRODUCING PURIFIED AMINE COMPOUND

TECHNICAL FIELD

The present invention relates to a method for producing a purified form of an amine compound.

BACKGROUND ART

Patent Document 1 discloses that an amine compound represented by the formula (1) is useful as an intermediate for an N-indanyl carboxamide compound which shows antifungal activity:

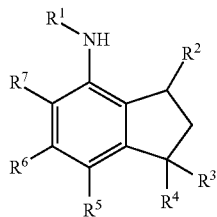
(1)

wherein $R^1$, $R^2$, $R^3$, $R^4$, $R^5$, $R^6$ and $R^7$ each independently represent a hydrogen atom or a hydrocarbon group.

PRIOR ART DOCUMENT

Patent Document

Patent Document 1: JP-A-07-215921

SUMMARY OF THE INVENTION

Problem to be Solved by the Invention

In order to produce a highly pure N-indanyl carboxamide compound industrially, it is important to obtain a highly pure amine compound represented by the formula (1). However, no method has been known for producing the highly pure amine compound represented by the formula (1).

Means for Solving the Problem

The present invention includes the following aspects and embodiments thereof:

[1] A method for producing a purified amine compound represented by the formula (1):

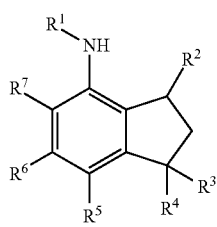
(1)

wherein $R^1$, $R^2$, $R^3$, $R^4$, $R^5$, $R^6$ and $R^7$ each independently represent a hydrogen atom or a hydrocarbon group, comprising:

step (A): reacting a crude amine compound represented by the formula (1) with a hydrogen halide in the presence of water and an organic solvent insoluble in water;

step (B): separating a phase in which a hydrogen halide salt of the amine compound represented by the formula (1) produced in step (A) is dissolved from the other phase(es);

step (C): precipitating the hydrogen halide salt of the amine compound represented by the formula (1) from the phase obtained in step (B) in which the hydrogen halide salt of the amine compound represented by the formula (1) is dissolved; and step (D): isolating the hydrogen halide salt of the amine compound represented by the formula (1) precipitated in step (C), and reacting the salt with a base.

[2] The production method according to item [1], wherein the hydrogen halide is hydrogen chloride.

[3] The production method according to item [1] or [2], wherein in step (B), the phase in which the hydrogen halide salt of the amine compound represented by the formula (1) is dissolved is an organic phase.

[4] The production method according to item [3], wherein the concentration of halide ion in a water phase is 0.8 mol/L or more.

[5] A hydrogen halide salt of an amine compound represented by the formula (1):

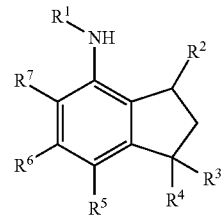
(1)

wherein $R^1$, $R^2$, $R^3$, $R^4$, $R^5$, $R^6$ and $R^7$ each independently represent a hydrogen atom or a hydrocarbon group.

[6] A method for producing a compound represented by the formula (2):

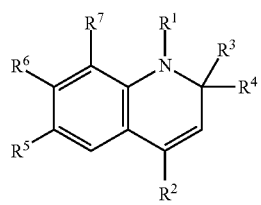
(2)

wherein $R^1$, $R^2$, $R^3$, $R^4$, $R^5$, $R^6$ and $R^7$ each independently represent a hydrogen atom or a hydrocarbon group, including depolymerizing an oligomer made from the compound represented by the formula (2).

[7] The production method according to item [6], wherein the reaction is conducted by adding an acid catalyst to the oligomer made from the compound represented by the formula (2) and distilling off under reduced pressure.

Effect of the Invention

A highly pure amine compound represented by the formula (1) can be produced by the present invention.

MODE FOR CARRYING OUT THE INVENTION

A description will be made to the amine compound represented by the formula (1) (hereinafter referred to as Amine Compound (1)).

Examples of the hydrocarbon group include alkyl groups having 1 to 20 carbon atoms, such as methyl, ethyl, propyl, isopropyl, butyl, isobutyl, tert-butyl, pentyl, hexyl, nonyl, decyl, and 3,7-dimethyloctyl groups; and cycloalkyl groups having 3 to 20 carbon atoms, such as cyclopentyl, cyclohexyl, and norbornyl groups. Of these groups, preferred are alkyl groups having 1 to 6 carbon atoms, and cycloalkyl groups having 3 to 6 carbon atoms; more preferred are alkyl groups having 1 to 6 carbon atoms, and cyclopentyl and cyclohexyl groups; even more preferred are alkyl groups having 1 to 4 carbon atoms; and even much more preferred are methyl, ethyl and propyl groups.

$R^1$ is preferably a hydrogen atom, an alkyl group having 1 to 6 carbon atoms, or a cycloalkyl group having 3 to 6 carbon atoms, more preferably a hydrogen atom, or an alkyl group having 1 to 4 carbon atoms, even more preferably a hydrogen atom, or a methyl, ethyl or propyl group, even much more preferably a hydrogen atom.

$R^2$ is preferably an alkyl group having 1 to 6 carbon atoms, or a cycloalkyl group having 3 to 6 carbon atoms, more preferably an alkyl group having 1 to 4 carbon atoms, even more preferably a methyl, ethyl or propyl group, even much more preferably a methyl group.

$R^3$ and $R^4$ are each independently preferably an alkyl group having 1 to 6 carbon atoms, or a cycloalkyl group having 3 to 6 carbon atoms, more preferably an alkyl group having 1 to 4 carbon atoms, even more preferably a methyl, ethyl or propyl group. $R^3$ and $R^4$ are even much more preferably each a methyl group.

$R^5$, $R^6$ and $R^7$ are each independently preferably a hydrogen atom, an alkyl group having 1 to 6 carbon atoms, or a cycloalkyl group having 3 to 6 carbon atoms, more preferably a hydrogen atom, or an alkyl group having 1 to 4 carbon atoms, even more preferably a hydrogen atom, or a methyl, ethyl or propyl group, even much more preferably a hydrogen atom.

Examples of the amine compound (1) include 4-amino-1,1,3-trimethylindane, 4-amino-1,1,3-triethylindane, 4-amino-1,1,3,7-tetramethylindane, 4-amino-1,1,3,5,7-pentamethylindane, 4-amino-1,1,3,5,6,7-hexamethylindane, and 4-methylamino-1,1,3-trimethylindane.

Step (A) is a step of reacting a crude amine compound (1) with a hydrogen halide in the presence of water and an organic solvent insoluble in water.

The amine compound (1) can be obtained by hydrogenating a compound represented by the formula (2) to yield a compound represented by the formula (3):

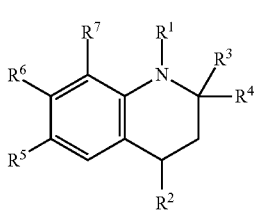

(3)

wherein $R^1$, $R^2$, $R^3$, $R^4$, $R^5$, $R^6$ and $R^7$ each represent the same meaning as described above; and reacting the compound represented by the formula (3) with an acid. The amine compound (1) in which $R^1$ is a hydrogen atom can be obtained by reacting a compound represented by the formula (2) with a protecting reagent such as acetic anhydride to yield a compound represented by the formula (2) in which the nitrogen atom is protected with a protecting group, hydrogenating the resulting compound represented by the formula (2) in which the nitrogen atom is protected with the protecting group to yield a compound represented by the formula (3) in which the nitrogen atom is protected with the protecting group, and then reacting an acid with the compound represented by the formula (3) in which the nitrogen atom is protected with the protecting group. The acid is preferably sulfuric acid. The sulfuric acid concentration is usually from 92 to 98 wt. %. From the viewpoint of the yield, the concentration is preferably from 92 to 97 wt. %. The reaction between the compound represented by the formula (3) and the acid is conducted in the absence of a solvent. The reaction temperature is usually from 20 to 80° C. After completion of the reaction, the resultant reaction mixture is mixed with water, and the resultant mixture is neutralized with an alkali, extracted with an organic solvent insoluble in water, such as toluene, to yield a solution containing the crude amine compound (1). The solution may be used as it is in the present invention. Alternatively, after the solvent is removed from the solution, the resultant may be used in the invention. Purity of the amine compound (1) in the crude amine compound (1) is usually 75 to 97%.

The compound represented by the formula (2) can be obtained by depolymerizing the oligomer made from the compound represented by the formula (2).

Examples of the oligomer made from the compound represented by the formula (2) are ANTIGEN FR or ANTIGEN RD (manufactured by Sumitomo Chemical Co., Ltd.).

The depolymerization is conducted by reacting the compound represented by the formula (2) with an acid catalyst.

Examples of the acid catalyst include hydrochloric acid, sulfuric acid, nitric acid, tetrafluoroboric acid, p-toluenesulfonic acid, and p-toluenesulfonic acid hydrate. Preferred is p-toluenesulfonic acid monohydrate.

The use amount of the p-toluenesulfonic acid compound is usually from 0.1 to 30 parts by weight, preferably from 0.1 to 20 parts by weight, more preferably from 1 to 10 parts by weight per 100 parts by weight of the oligomer made from the compound represented by the formula (2).

The reaction temperature is usually from 100 to 250° C., preferably from 120 to 230° C., even more preferably from 140 to 200° C.

The reaction may be conducted under a normal pressure or under a reduced pressure. The reaction is preferably conducted under a reduced pressure. When the reaction is conducted under a pressurized pressure, the pressure is usually from 0.1 to 10 kPa, preferably from 0.3 to 7 kPa, more preferably from 0.5 to 5 kPa.

The reaction is conducted preferably in the absence of a solvent.

It is preferred to conduct the depolymerization while the resultant compound represented by the formula (2) is distilled off from the reaction system under a reduced pressure. The obtained compound has relatively high purity.

Examples of the organic solvent insoluble in water include an aliphatic hydrocarbon solvent such as hexane or heptane, an aromatic hydrocarbon solvent such as toluene or xylene, a hydrophobic ester solvent such as ethyl acetate, a hydrophobic ether solvent such as diethyl ether or methyl cyclopentyl ether, and a hydrophobic ketone solvent such as methyl tert-butyl ketone. Preferred are the aliphatic hydrocarbon solvent and the aromatic hydrocarbon solvent, and preferred is the aromatic hydrocarbon solvent.

The ratio of the use amount of water to that of the organic solvent insoluble in water (ratio by weight:water/the organic solvent insoluble in water) is usually from 1/99 to 99/1, preferably from 5/95 to 95/5, more preferably from 10/90 to 90/10.

Examples of the hydrogen halide include hydrogen chloride, hydrogen bromide, and hydrogen iodide. Preferred are hydrogen chloride and hydrogen bromide, and more preferred is hydrogen chloride. The hydrogen halide may be used as it is, or may be used in a form of an aqueous solution thereof. When the aqueous solution of the hydrogen halide is used, the use amount of water can be determined by considering the amount of water in the aqueous solution.

The use amount of the hydrogen halide is usually 1 mole or more per mole of the amine compound (1). The upper limit thereof is not restricted. However, from the viewpoint of practical use, the use amount is 2 moles or less per mole of the amine compound (1).

The reaction between the amine compound (1) and the hydrogen halide is usually conducted by mixing the amine compound (1) with the hydrogen halide. The order of the mixing is not restricted.

The reaction temperature is usually from 0 to 100° C., preferably from 5 to 90° C., more preferably from 10 to 80° C.

The reaction time is usually from 0.1 to 24 hours, preferably from 0.1 to 12 hours, more preferably from 0.1 to 6 hours.

Step (B) is a step of separating a phase in which a hydrogen halide salt of the amine compound (1) produced in step (A) is dissolved from the other phase(es).

After completion of step (A), for example, the resultant mixture is allowed to stand still and subjected to liquid phase separating treatment, thereby the phase in which a hydrogen halide salt of the amine compound (1) is dissolved is separated from the other phase(es). When the separated phase is the organic phase in which the hydrogen halide salt of the amine compound (1) is dissolved, the organic phase may be washed with water, if necessary. When the separated phase in which the hydrogen halide salt of the amine compound (1) is dissolved is a water phase, the water phase may be washed with the above-mentioned organic solvent insoluble in water if necessary.

When the use amount of the hydrogen halide in step (A) is 1.15 moles or more, preferably 1.2 moles or more per mole of the amine compound (1), the resulting hydrogen halide salt of the amine compound (1) is usually dissolved in the organic phase. When the use amount of the hydrogen halide is less than 1.15 moles per mole of the amine compound (1), the resulting hydrogen halide salt of the amine compound (1) is usually dissolved in the water phase. For this reason, by the adjustment of the use amount of the hydrogen halide in step (A), the phase in which the hydrogen halide salt of the amine compound (1) is to be dissolved is controllable.

When the concentration of the halide ion in the water phase of the mixture obtained in step (A) is 0.8 mol/L or more, the hydrogen halide salt of the amine compound (1) is usually soluble in the organic phase. When the concentration of the halide ion in the water phase of the mixture obtained in step (A) is less than 0.8 mol/L, the hydrogen halide salt of the amine compound (1) is usually dissolved in the water phase. For this reason, by adjusting the concentration of the halide ions in the water phase of the mixture, the phase in which the hydrogen halide salt of the amine compound (1) is to be dissolved is controllable. The method for adjusting the concentration of the halide ions in the water phase may be a method of mixing the mixture yielded in step (A) with a water-soluble inorganic halide such as sodium chloride.

The temperature at which the phase in which the hydrogen halide salt of the amine compound (1) is dissolved is separated from the other phase (es) is usually from 0 to 100° C., preferably from 5 to 90° C., more preferably from 10 to 80° C.

Step (C) is a step of precipitating the hydrogen halide salt of the amine compound (1) from the phase obtained in step (B) in which the hydrogen halide salt of the amine compound (1) is dissolved.

The precipitated hydrogen halide salt of the amine compound (1) can be isolated, for example, by cooling the phase in which the hydrogen halide salt of the amine compound (1) is dissolved as it is, or after concentration of the phase.

The cooling temperature is preferably a temperature at least 5° C. lower than the separating temperature in step (B), more preferably at from −15 to 50° C., even more preferably at from −5 to 40° C., even still more preferably at from 0 to 30° C. The cooling period is usually from 1 minute to 24 hours.

Step (D) is a step of isolating the hydrogen halide salt of the amine compound (1) precipitated in step (C), and reacting the salt with a base. In step (C), a purified amine compound (1) is obtained.

The precipitated hydrogen halide salt of the amine compound (1) can be isolated, for example, by filtrating the mixture in which the salt is precipitated. The isolated hydrogen halide salt of the amine compound (1) may be washed with an appropriate solvent if necessary.

Examples of the base include ammonia; an alkali metal hydroxide such as lithium hydroxide, sodium hydroxide, or potassium hydroxide; an alkaline earth metal hydroxide such as magnesium hydroxide, calcium hydroxide, or barium hydroxide; an alkali metal hydrogencarbonate such as sodium hydrogencarbonate or potassium hydrogencarbonate; an alkali metal carbonate such as sodium carbonate or potassium carbonate; and an organic bases such as trimethylamine, triethylamine, ethyldiisopropylamine, pyridine, or quinoline. Of these bases, preferred are ammonia, sodium hydroxide, potassium hydroxide, calcium hydroxide, barium hydroxide, sodium hydrogencarbonate, trimethylamine, triethylamine, and pyridine. More preferred are ammonia, sodium hydroxide, potassium hydroxide, and sodium hydrogencarbonate. Even more preferred are sodium hydroxide and potassium hydroxide. These bases may each be used as it is, or may be used in the form of a solution thereof, such as an aqueous solution thereof.

The reaction between the hydrogen halide salt of the amine compound (1) and the base is usually conducted by mixing the two with each other. The reaction is preferably conducted in water.

The use amount of the base is usually 1 mole or more per mole of the hydrogen halide salt of the amine compound (1). The upper limit thereof is not restricted. However, from the viewpoint of practical use, the amount is 2 moles or less per mole of the hydrogen halide salt of the amine compound (1).

The reaction temperature is usually from 0 to 100° C. The reaction time is usually from 0.1 to 5 hours.

After completion of the reaction, for example, the reaction mixture is mixed with an organic solvent insoluble in water to obtain an organic phase, and the organic phase is concentrated to yield a purified amine compound (1). In the present specification, the "purified amine compound (1)" means an amine compound (1) of higher purity than the crude amine compound (1). The purity of the purified amine compound (1) is usually 97.5% or more.

EXAMPLES

Hereinafter, the present invention will be described in more detail by way of working examples thereof.

Example 1

Under a nitrogen atmosphere, 203.8 g of an oligomer made from 2,2,4-trimethyl-1,2-dihydroquinoline and 6.8 g of p-toluenesulfonic acid monohydrate were added into a flask. The pressure in the flask was adjusted to 3 kPa and then the resultant mixture was heated to 170° C. to yield 174.6 g of 2,2,4-trimethyl-1,2-dihydroquinoline. Yield: 82.2%, purity: 95.9%.

Reference Example 1-1

Under a nitrogen atmosphere, 89.3 g of 2,2,4-trimethyl-1,2-dihydroquinoline and 16.9 g of sodium acetate were added into a flask. The resultant mixture was heated to 120° C., and then thereto was dropwise added 90 g of acetic anhydride. The resultant mixture was kept at 120° C. for 8 hours, and then cooled. To the resultant reaction mixture was added 133.4 g of toluene, and thereto was dropwise added 177.8 g of 27 wt. % aqueous sodium hydroxide solution. Phase separation of the resultant mixture gave 240.3 g of a toluene solution containing 1-acetyl-2,2,4-trimethyl-1,2-dihydroquinoline. Content: 42.7 wt. %, yield: 95.2%, purity: 97.1%.

Reference Example 1-2

Into a flask were added 267.8 g of a toluene solution containing 1-acetyl-2,2,4-trimethyl-1,2-dihydroquinoline (content: 36.8 wt. %, purity: 96.7%) and 3.92 g of 5 wt. % palladium/carbon. The inside of the flask was pressurized with hydrogen, and then the resultant mixture was heated at 40° C. After completion of the reaction, the reaction mixture was filtrated, and the resultant filtrate was concentrated to yield 100.5 g of 1-acetyl-2,2,4-trimethylytetrahydroquinoline. Yield: 95.9, purity: 98.1%.

Reference Example 1-3

Under a nitrogen atmosphere, 125.2 g of 1-acetyl-2,2,4-trimethylytetrahydroquinoline was heated to 90° C., and then 184.8 g of 98 wt. % sulfuric acid was dropwise added thereto. The resultant mixture was kept at 60° C. The resultant reaction mixture was dropwise added to hot water of 98° C. The resultant mixture was heated to 105° C., and then kept at the same temperature for 4 hours. The resultant mixture was dropwise added to 623.4 g of 27 wt. % aqueous sodium hydroxide solution to neutralize the mixture. The resultant was then subjected to extraction with toluene to yield 190.4 g of a toluene solution containing crude 4-amino-1,1,3-trimethylindane. Content: 39.1%, purity: 92.6%, yield: 76.4%.

Reference Example 1-4

Under a nitrogen atmosphere, 110 g of 1-acetyl-2,2,4-trimethylytetrahydroquinoline was heated to 90° C., and then dropwise added to 166 g of 96 wt. % sulfuric acid. The resultant mixture was kept at 60° C. The resultant reaction mixture was dropwise added to hot water of 98° C. The resultant mixture was heated to 105° C., and then kept at the same temperature for 4 hours. The resultant mixture was dropwise added to 550.2 g of 27 wt. % aqueous sodium hydroxide solution to neutralize the mixture. The resultant was then subjected to extraction with toluene to yield 106.3 g of a toluene solution containing crude 4-amino-1,1,3-trimethylindane. Content: 69.0%, purity: 92.5%, yield: 85.7%.

Example 2

Under a nitrogen atmosphere, 158.5 g of a toluene solution containing crude 4-amino-1,1,3-trimethylindane (purity: 88.5%) (content: 25.2%), 41.8 g of toluene, and 18.0 g of water were added into a flask. The resultant mixture was heated to 70° C., and then thereto was added 36.5 g of concentrated hydrochloric acid. The resultant mixture was stirred at 70° C. for 1 hour. The resultant mixture was allowed to stand still and a water phase and an organic phase in which 4-amino-1,1,3-trimethylindane hydrochloride was dissolved were separated. While the organic phase was stirred, the phase was cooled to 5° C. to precipitate crystals of 4-amino-1,1,3-trimethylindane hydrochloride. The precipitated crystal was isolated by filtration to obtain 4-amino-1,1,3-trimethylindane hydrochloride. Melting point: 228 to 229° C.

The collected 4-amino-1,1,3-trimethylindane hydrochloride was dissolved in hot water. To the resultant solution was added an aqueous sodium hydroxide solution. Toluene was added to the resultant mixture, and then the resultant organic phase was separated therefrom. The organic phase was washed with water, and then concentrated under a reduced pressure to yield 36.9 g of 4-amino-1,1,3-trimethylindane as a liquid of light brown color. Yield: 92.2%, purity: 99.8%.

Example 3

Under a nitrogen atmosphere, 43.62 g of a toluene solution containing crude 4-amino-1,1,3-trimethylindane (purity: 87.0%) (content: 49.7%), 65.0 g of toluene, and 9.78 g of water were added into a flask. The resultant mixture was heated to 70° C., and then thereto was added 13.5 g of concentrated hydrochloric acid. The resultant mixture was stirred at 70° C. for 1 hour. Thereto was then added 1.81 g of sodium chloride, and the resultant was stirred. The resultant mixture was allowed to stand still and a water phase and an organic phase in which 4-amino-1,1,3-trimethylindane hydrochloride was dissolved were separated. While the organic phase was stirred, the phase was cooled to 5° C. to precipitate crystals of 4-amino-1,1,3-trimethylindane hydrochloride. The precipitated crystal was isolated by filtration to obtain 4-amino-1,1,3-trimethylindane hydrochloride. Melting point: 228 to 229° C.

The resultant 4-amino-1,1,3-trimethylindane hydrochloride was dissolved in hot water. To the resultant solution was added a sodium hydroxide solution in water. Toluene was added to the resultant mixture, and then the resultant organic phase was separated therefrom. The organic phase was washed with water, and then concentrated under a reduced pressure to yield 22.4 g of 4-amino-1,1,3-trimethylindane as a liquid of light brown color. Yield: 93.2%, purity: 99.7%.

Example 4

Under a nitrogen atmosphere, 96.9 g of a toluene solution containing crude 4-amino-1,1,3-trimethylindane (purity:

87.1%) (content: 39.4%) and 38.2 g of water were added into a flask. The resultant mixture was heated to 70° C., and then thereto was added 23.8 g of concentrated hydrochloric acid. The resultant mixture was stirred at 70° C. for 1 hour. The resultant mixture was allowed to stand still and an organic phase and a water phase in which 4-amino-1,1,3-trimethylindane hydrochloride was dissolved were separated. While the water phase was stirred, the phase was cooled to 5° C. to precipitate crystals of 4-amino-1,1,3-trimethylindane hydrochloride. The precipitated crystal was isolated by filtration to give 4-amino-1,1,3-trimethylindane hydrochloride. Melting point: 228 to 229° C.

The resultant 4-amino-1,1,3-trimethylindane hydrochloride was dissolved in hot water. To the resultant solution was added an aqueous sodium hydroxide solution. Toluene was added to the resultant mixture, and then the resultant organic phase was separated therefrom. The organic phase was washed with water, and then concentrated under a reduced pressure to yield 33.6 g of 4-amino-1,1,3-trimethylindane as a liquid of a light brown color. Yield: 88.0%, purity: 99.6%.

Example 5

Under a nitrogen atmosphere, a crude optically active 4-amino-1,1,3-trimethylindane (purity: 96.7%; enantiomeric excess: 12.6%), 71.7 g of toluene and 8.14 g of water were added into a flask. The resultant mixture was heated to 70° C., and then thereto was added 14.0 g of concentrated hydrochloric acid. The resultant mixture was stirred at 70° C. for 1 hour. The resultant mixture was allowed to stand still and a water phase and an organic phase in which 4-amino-1,1,3-trimethylindane hydrochloride was dissolved were separated. While the organic phase was stirred, the phase was cooled to 5° C. to precipitate crystals of 4-amino-1,1,3-trimethylindane hydrochloride. The precipitated crystal was isolated by filtration to give 4-amino-1,1,3-trimethylindane hydrochloride. Melting point: 228 to 229° C.

The resultant 4-amino-1,1,3-trimethylindane hydrochloride was dissolved in hot water. To the resultant solution was added an aqueous sodium hydroxide solution. Toluene was added to the resultant mixture, and then the resultant organic phase was separated therefrom. The organic phase was washed with water, and then concentrated under a reduced pressure to yield 14.4 g of 4-amino-1,1,3-trimethylindane as a liquid of a light brown color. Yield: 79.5%, purity: 99.8%, enantiomeric excess: 0.66%.

Example 6

Under a nitrogen atmosphere, 225.6 g of a toluene solution containing crude 4-amino-1,1,3-trimethylindane (purity: 88.5%) (content: 42.0%), 90.2 g of toluene and 18.0 g of water were added into a flask. The resultant mixture was heated to 65° C., and then thereto was added 120.9 g of 47% hydrobromic acid. The resultant mixture was stirred at 65° C. for 1 hour. The resultant mixture was allowed to stand still and a water phase and an organic phase in which 4-amino-1,1,3-trimethylindane hydrobromide was dissolved were separated. While the organic phase was stirred, the phase was cooled to 10° C. to precipitate crystals of 4-amino-1,1,3-trimethylindane hydrobromide. The precipitated crystal was isolated by filtration to give 4-amino-1,1,3-trimethylindane hydrobromide. Melting point: 199 to 200° C.

The resultant 4-amino-1,1,3-trimethylindane hydrobromide was dissolved in hot water to prepare an aqueous solution. To the solution was added an aqueous sodium hydroxide solution. Toluene was added to the resultant mixture, and then the resultant organic phase was separated therefrom. The organic phase was washed with water, and then concentrated under a reduced pressure to yield 4-amino-1,1,3-trimethylindane as a liquid of a light brown color. Yielded amount: 132.57 g, yield: 90.0%, purity: 99.3%.

Comparative Example 1

Under a nitrogen atmosphere, 62.5 g of a toluene solution containing crude 4-amino-1,1,3-trimethylindane (purity: 87%) (content: 39.4%) was added into a flask and was cooled to 5° C. Thereto was then dropwise added 18.4 g of concentrated hydrochloric acid. The resultant mixture was filtrated to isolate 4-amino-1,1,3-trimethylindane hydrochloride.

The obtained 4-amino-1,1,3-trimethylindane hydrochloride was dissolved in hot water. To the resultant solution was added an aqueous sodium hydroxide solution. Toluene was added to the resultant mixture, and then the resultant organic phase was separated therefrom. The organic phase was washed with water, and then concentrated under a reduced pressure to yield 23.1 g of 4-amino-1,1,3-trimethylindane as a liquid of a brown color. Purity: 94.4%.

Comparative Example 2

Under a nitrogen atmosphere, 110.2 g of a toluene solution containing crude 4-amino-1,1,3-trimethylindane (purity: 87.6%) (content: 39.5%) was added into a flask. The pressure inside the flask was reduced to 10 kPa, and was heated to 60° C. to evaporate toluene. Furthermore, the pressure was reduced to 2.0 kPa, and then heated to 140° C. to yield 39.9 g of 4-amino-1,1,3-trimethylindane as a liquid of a light brown color. Yield: 87.0%, purity: 92.5%.

INDUSTRIAL APPLICABILITY

A highly pure amine compound represented by the formula (1) can be produced by the present invention.

The invention claimed is:
1. A method for producing a purified amine compound represented by the formula (1):

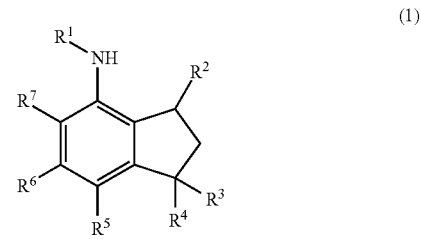

(1)

wherein $R^1$, $R^5$, $R^6$ and $R^7$ each independently represent a hydrogen atom or a hydrocarbon group, and
$R^2$, $R^3$ and $R^4$ each independently represent an alkyl group having 1 to 6 carbon atoms, or a cycloalkyl group having 3 to 6 carbon atoms,
comprising:
step (A): reacting a crude amine compound represented by the formula (1) with a hydrogen halide in the presence of water and an organic solvent insoluble in water;

step (B): separating a phase in which a hydrogen halide salt of the amine compound represented by the formula (1) produced in step (A) is dissolved from the other phase(es);

step (C): precipitating the hydrogen halide salt of the amine compound represented by the formula (1) from the phase obtained in step (B) in which the hydrogen halide salt of the amine compound represented by the formula (1) is dissolved; and step (D): isolating the hydrogen halide salt of the amine compound represented by the formula (1) precipitated in step (C), and reacting the salt with a base.

2. The production method according to claim 1, wherein the hydrogen halide is hydrogen chloride.

3. The production method according to claim 1, wherein in step (B), the phase in which the hydrogen halide salt of the amine compound represented by the formula (1) is dissolved is an organic phase.

4. The production method according to claim 3, wherein the concentration of the halide ion in a water phase is 0.8 mol/L or more.

* * * * *